(12) United States Patent
Pasco et al.

(10) Patent No.: US 7,196,072 B2
(45) Date of Patent: Mar. 27, 2007

(54) **HIGH MOLECULAR WEIGHT POLYSACCHARIDE FRACTION FROM *ALOE VERA* WITH IMMUNOSTIMULATORY ACTIVITY**

(75) Inventors: David Stanley Pasco, Oxford, MS (US); Nirmal Derek Ceri Pugh, Oxford, MS (US); Mahmoud ElSohly, Oxford, MS (US); Samir Ross, Oxford, MS (US)

(73) Assignee: University of Mississippi, University, MS (US)

( * ) Notice: Subject to any disclaimer, the term of this patent is extended or adjusted under 35 U.S.C. 154(b) by 149 days.

(21) Appl. No.: 10/332,408

(22) PCT Filed: Jul. 9, 2001

(86) PCT No.: PCT/US01/21596

§ 371 (c)(1),
(2), (4) Date: Aug. 13, 2003

(87) PCT Pub. No.: WO02/03999

PCT Pub. Date: Jan. 17, 2002

(65) Prior Publication Data

US 2004/0038931 A1 Feb. 26, 2004

Related U.S. Application Data

(60) Provisional application No. 60/217,002, filed on Jul. 10, 2000.

(51) Int. Cl.
*A61K 31/715* (2006.01)
*C08B 37/00* (2006.01)

(52) U.S. Cl. .......................... 514/54; 514/53; 536/55.1; 536/127; 536/123; 536/123.1; 536/124

(58) Field of Classification Search ................ 536/123, 536/128, 55.1, 127, 123.1, 124; 514/53, 514/54
See application file for complete search history.

(56) References Cited

U.S. PATENT DOCUMENTS

| | | | | |
|---|---|---|---|---|
| 4,511,559 A | * | 4/1985 | Szendrei et al. | 514/54 |
| 4,735,935 A | * | 4/1988 | McAnalley | 514/53 |
| 6,133,440 A | * | 10/2000 | Qiu et al. | 536/123 |
| 6,482,942 B1 | * | 11/2002 | Vittori | 536/128 |

OTHER PUBLICATIONS

Qiu et al. Modified *Aloe barbadensis* Polysaccharide with Immunoregulatory Activity. Planta Med. Mar. 2000; 66(2):152-6.*

* cited by examiner

*Primary Examiner*—Shaojia Anna Jiang
*Assistant Examiner*—Devesh Khare
(74) *Attorney, Agent, or Firm*—Eugene C. Rzucidlo; Hunton & Williams LLP

(57) ABSTRACT

A complex, water soluble polysaccharide fraction having potent immunostimulatory activity isolated from *Aloe vera*. The polysaccharide fraction has an apparent molecular weight above 2 million daltons. Its major glycosyl components are glucose, galactose, mannose and arabinose. The invention further includes pharmaceutical compositions containing the instant polysaccharide fraction, optionally in combination with acceptable pharmaceutical carriers and/or excipients. These pharmaceutical compositions may be used to provide immunostimulation to an individual in need of such treatment by administering to such an individual an effective amount of the composition. The polysaccharide fraction is also useful as a component of dietary supplements and as a standardization component of commercial *Aloe* products.

18 Claims, 4 Drawing Sheets

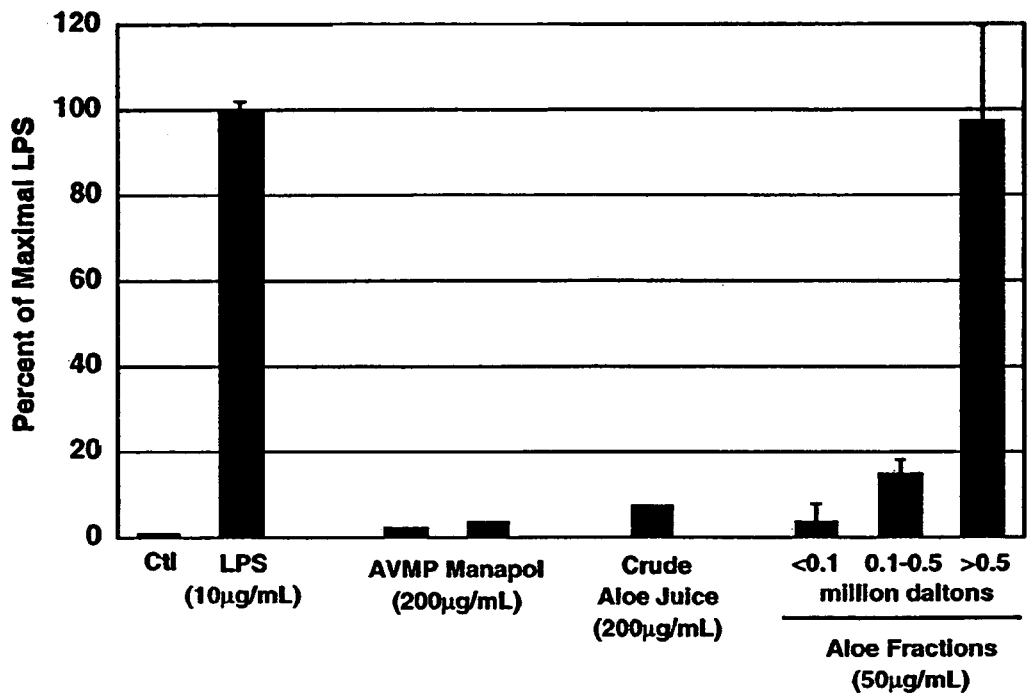

FIG. 1. Evaluation and comparison of AVMP and Manapol with crude aloe vera fractions. AVMP and Manapol cause weak activation of NF-kappa B directed luciferase expression in THP-1 cells at 200μg/mL. In contrast, the high molecular weight fraction (>500,000 daltons) from crude aloe vera juice exhibits potent immunostimulatory activity at 50μg/mL that is equivalent to levels achieved by maximal concentrations of LPS (10μg/mL). Samples run in duplicate in one experiment (means ± range).

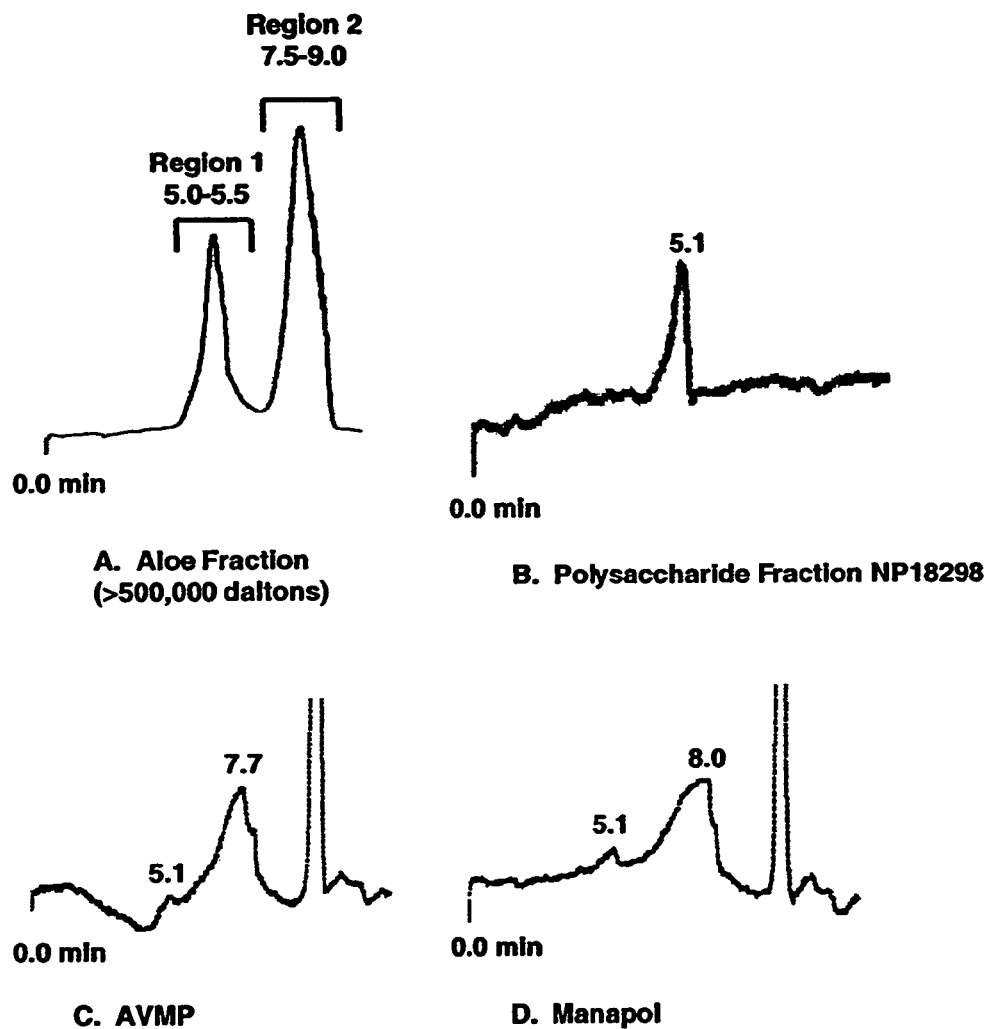
FIG. 2. Size exclusion HPLC chromatograms: 2a) aloe vera juice high molecular weight fraction (> 500,000 daltons), 75μL injection at 10mg/mL; 2b) polysaccharide fraction NP18298, 20μL injection at 1.8mg/mL; 2c) AVMP, 100μL injection at 1mg/mL; 2d) Manapol, 100μL injection at 1mg/mL.

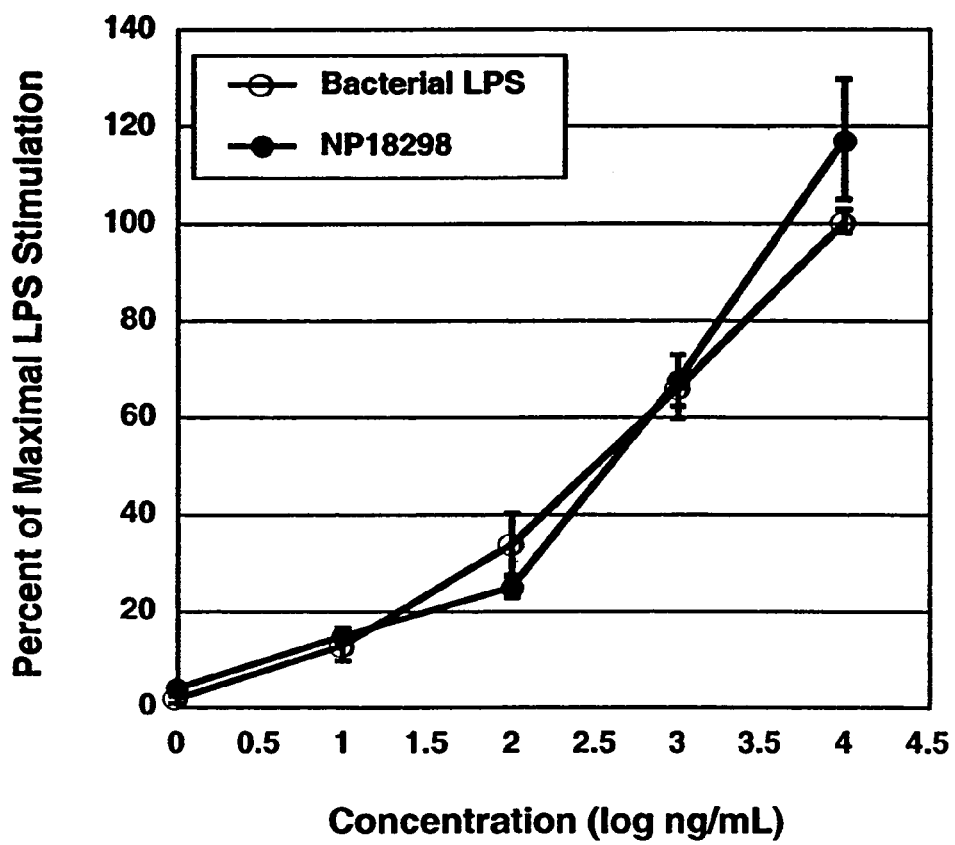
FIG. 3. Dose response for polysaccharide fraction NP18298 and bacterial LPS for activation of NF-kappa B in THP-1 monocytes/macrophages at 4-hours. Samples run in quadruplicate (means ± standard deviation).

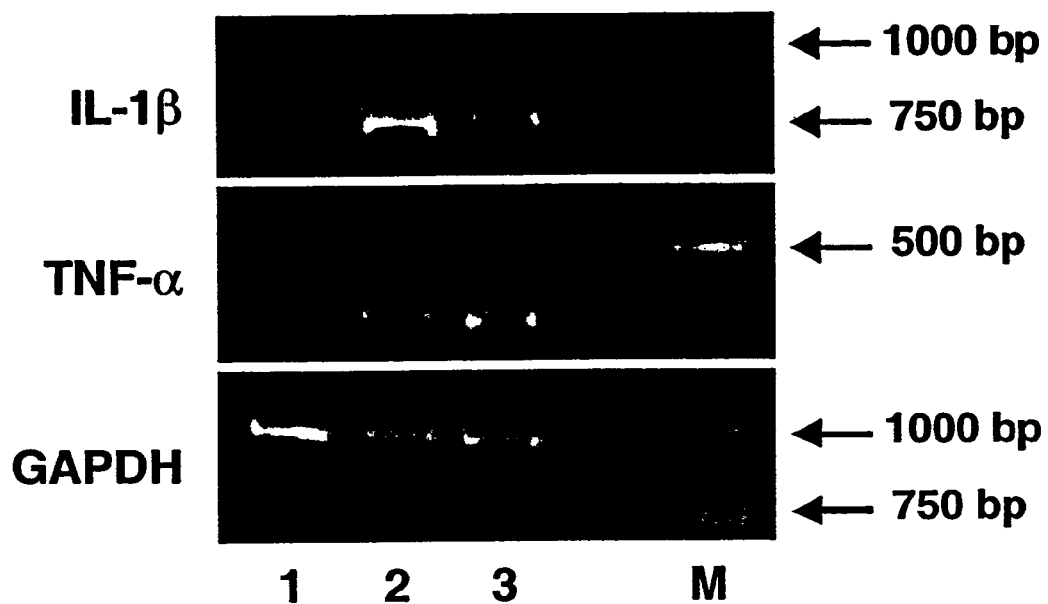
FIG. 4. Polysaccharide fraction NP18298 enhances proinflammatory cytokine production. RT-PCR results for IL-1β mRNA, TNF-α mRNA and GAPDH mRNA in THP-1 cells at 2 hours: (1) control, (2) bacterial LPS at 10μg/mL, (3) polysaccharide fraction NP18298 at 10μg/mL, and (M) PCR Marker.

HIGH MOLECULAR WEIGHT POLYSACCHARIDE FRACTION FROM *ALOE VERA* WITH IMMUNOSTIMULATORY ACTIVITY

FIELD OF THE INVENTION

This invention relates to the isolation and structural characterization of a potent, water soluble immunostimulatory polysaccharide fraction from *aloe vera* (*Aloe barbadensis*) juice having an apparent molecular weight above 2 million daltons. It further relates to methods for the treatment and/or prevention of a variety of disease conditions using the material of this invention.

BACKGROUND OF THE INVENTION

The genus *Aloe* (Liliaceae) is a shrubby tropical/subtropical plant which has succulent and elongate leaves. Of the more than 360 *Aloe* species known, *Aloe barbadensis* Miller (*Aloe vera* Linne) is the most widely used, both commercially and for its therapeutic properties. *Aloe vera* plants contain two major juice materials: first, a yellow exudate containing a high concentration of anthraquinone compounds that has been used throughout the centuries as a cathartic and for medicinal purges; and second, a clear mucilaginous gel that has been used since ancient times to treat burns and other wounds where it is thought to increase the rate of healing and reduce the risk of infection. See Grindlay, D.; Reynolds, T., *J. Ethnopharmcol.* 1986, 16(2–3), 117–151; and Joshi, S. P., *J. Med. Aromat. Plant Sci.* 1998, 20(3), 768–773.

Several chemical components of the *Aloe* gel are thought to be responsible for its wound healing and immunostimulatory properties. For example, the glycoprotein Aloctin A is reported to have antitumor and antiulcer effects (see Imanishi, K., *Phyother. Res.* 1993, 7, S20–S22), and a 29KD glycoprotein has been found to increase proliferation of normal human dermal cells (see Yagi, A.; Egusa, T.; Arase, M.; Tanabe, M.; Tsuji, H., *Planta Med.* 1997, 63(1), 18–21). Clearly, however, the major composition of *Aloe* gel comprises a mucilage of polysaccharide substances. Most of these polysaccharides are glucomannans, mannans or pectins having a range of molecular weights. A major focus of research has been on the carbohydrate fraction isolated from *Aloe* gel known as, "acemannan" which comprises a polydispersed β-(1,4)-linked acetylated mannan interspersed with O-acetyl groups.

One mechanism by which *Aloe* components may enhance wound healing is by activation of macrophages. Monocytes/macrophages are found in practically every tissue of the body where they are critical in coordinating immune responses and numerous biological processes. (see Elgert, K. D.; Alleva, D. G.; Mullins, D. W., *J. Leukoc. Biol.* 1998, 64(3), 275–290). These cells function as phagocytes, i.e., debridement agents and they produce growth factors that influence the angiogenesis stage of wound repair, (see Wilson, K., *Nurs. Crit. Care* 1997, 2(6), 291–296). The production of cytokines by macrophages requires activation of these cells and prolonged wound healing times in aged mammals may be symptomatic of impaired macrophage function, (see Ashcroft, G. S.; Horan, M. A.; Ferguson, M. W., *Lab. Invest.* 1998, 78(1), 47–58). In cancer, macrophages mediate tumor cytotoxicity functions through the production of cytokines and other immune factors (see Gordon, S., *Res. Immunol.* 1998, 149(7–8), 685–688). In order for macrophages to play a major role in adaptive and innate immunity they must respond effectively to environmental agents by first becoming activated (see Adams, D. O.; Hamilton, T. A., In The Natural Immune System: The Macrophage; Lewis, C. E., McGee, J. O'D., Eds.; Oxford University Press Inc.: New York, 1992; pp 75–114). Macrophage activation is mediated by proinflammatory transcription factors such as nuclear factor kappa B (NF-kappa B). Such transcription factors then control and modulate the activation/repression of an array of genes that mediate a variety of immune responses.

In unstimulated macrophages, NF-kappa B exists as inactive heterodimers sequestered by inhibitory-kappa B (I-kappa B) proteins within the cytosol. Agents that cause I-kappa B proteins to dissociate and degrade allow for the translocation of NF-kappa B dimers to the nucleus where they can activate transcription of downstream genes (see May, M. J.; Ghosh, S., *Immunol. Today* 1998, 19(2), 80–88). Target genes regulated by NF-kappa B include proinflammatory cytokines, chemokines, inflammatory enzymes, adhesion molecules and receptors (see Baeuerle, P. A.; Henkel, T., *Annu. Rev. Immunol.* 1994, 12, 141–179).

Pharmacological activities of acemannan include antiviral effects, (see Sheets, M. A.; Unger, B. A.; Giggleman, G. F. Jr.; Tizard, I. R., *Mol. Biother.* 1991, 3(1), 41–45), activation of macrophages (see Zhang, L.; Tizard, I. R., *Immunopharmacology* 1996, 35(2), 119–28), stimulation of T cells (see Womble, D.; Helderman, J. H., *Immunopharmacol. Immunotoxicol.* 1992, 14(1–2), 63–77) and induction of nitric oxide production (see Ramamoorthy, L.; Kemp, M. C.; Tizard, I. R., *Mol. Pharmacol.* 1996, 50(4), 878–884). Thus, acemannan exerts some of its therapeutic properties through macrophage activity. However, very high concentrations of acemannan, e.g., 200 to 2000 µg/mL (see Karaca, K.; Sharma, J. M.; Nordgren, R., *Int. J. Immunopharmac.* 1995, 17(3), 183–188) are typically required to achieve modest activation of macrophages. This indicates that acemannan is not very potent.

SUMMARY OF THE INVENTION

Preliminary findings suggested that detectable levels of immunostimulation in crude *aloe* juice and gel could not be accounted for by previously known *aloe* components. Commercial *aloe* preparations (200 µg/mL) only resulted in negligible NF-kappa B activation in the macrophage assay. Therefore, the objective of the research was to isolate and characterize the material responsible for this observed immunostimulatory activity of crude *Aloe vera* juice.

This material was found to be a polysaccharide fraction (hereinafter referred to as "NP18298") having an apparent molecular weight above 2 million daltons. Its major glycosyl components are glucose (37.2%), galactose (23.9%), mannose (19.5%) and arabinose (10.3%). Immunostimulatory activity was measured using a transcription factor-based bioasssay for nuclear factor kappa B (NF-kappa B) activation in THP-1 human monocytes/macrophages. At 0.5 µg/mL, NP18298 robustly increased NF-kappa B directed luciferase expression to levels 50% of those achieved by maximal concentrations (10 µg/mL) of bacterial lipopolysaccharide (LPS). Reverse transcriptase-polymerase chain reaction demonstrated that polysaccharide fraction NP18298 induced the expression of the mRNAs encoding interleukin-1β (IL-1β) and tumor necrosis factor-α (TNF-α) to levels equal to those observed in cells maximally activated by LPS.

These results indicate that NP18298 is the most potent polysaccharide fraction characterized to this point and is most likely responsible for the majority of the macrophage activation properties of aloe. Although NP18298 comprises only 0.015% of the original dry weight of aloe juice, its potency for macrophage activation accounts fully for the immunostimulatory activity of the crude juice.

BRIEF DESCRIPTION OF THE FIGURES

FIG. 1 is a graph illustrating the evaluation and comparison of two commercial polysaccharide preparations (AVMP and Manapol) with crude aloe vera fractions. AVMP and Manapol cause weak activation of NF-kappa B directed luciferase expression in THP-1 cells at 200 µg/mL. In contrast, the high molecular weight fraction (>500,000 daltons) from crude aloe vera juice exhibits potent immunostimulatory activity at 50 µg/mL that is equivalent to levels achieved by maximal concentrations of LPS (10 µg/mL). The samples were run in duplicate in one experiment (mean±range).

FIG. 2 are size exclusion HPLC chromatograms: 2a) aloe vera juice high molecular weight fraction (>500,000 daltons), 75 µL injection at 10 mg/mL; 2b) polysaccharide fraction NP18298, 20 µL injection at 1.8 mg/mL; 2c) AVMP, 100 µL injection at 1 mg/mL; 2d) Manapol, 100 µL injection at 1 mg/mL.

FIG. 3 graphs the dose response for polysaccharide fraction NP18298 and bacterial LPS activation of NF-kappa B in THP-1 monocytes/macrophages at 4 hours. The samples were run in quadruplicate (mean±standard deviation).

FIG. 4 demonstrates that polysaccharide fraction NP18298 enhances proinflammatory cytokine production. Illustrated are RT-PCR results for IL-1β mRNA, TNF-α mRNA and GAPDH mRNA in THP-1 cells at 2 hours: (1) control, (2) bacterial LPS at 10 µg/mL, (3) polysaccharide fraction NP18298 at 10 µg/mL, and (M) PCR Marker.

EXPERIMENTAL SECTION

Materials. Aloe vera products (Aloe barbadensis) were purchased from the following sources: Nature's Sunshine Products Inc., Spanish Fork, Utah (whole leaf aloe juice, Lot Nos. 9120378A and 9080548A); Lily of the Desert Inc., Irving, Tex. (whole leaf aloe juice, Lot. No. B22908 and aloe gel, Lot No. B25809). Aloe vera mucilaginous polysaccharide (AVMP, Lot. No. 11586) and Manapol (Lot. No. 116018) were provided as a gift from Carrington Laboratories Inc. (Irving, Tex.). Aloe anthraquinones (aloin, aloe-emodin and emodin) were purchased from Sigma Chemical Co. (St. Louis, Mo.).

Bacterial lipopolysaccharide (E. coli, serotype 026:B6) was obtained from Sigma Chemical Co. THP-1 human monocytes were obtained from American Type Culture Collection (Rockville, Md.). LucLite™ luciferase reporter gene assay kit was purchased from Packard (Downers Grove, Ill.). NF-kappa B plasmid construct (pBIIXLUC) was a gift from Dr. Riccardo Dalla-Favera that contains two copies of NF-kappa B motif from HIV/IgK. See Chang, C. C.; Zhang, J.; Lombardi, L.; Neri, A.; Dalla-Favera, R., Oncogene 1994, 9(3), 923–933. Reverse Transcriptase (RT)-PCR kits were obtained from Promega (Madison, Wis.) and for RNA isolation the TRI Reagent® system was used (Molecular Research Center, Inc., Cincinnati, Ohio). RT-PCR primers for IL-1β, TNF-α and GAPDH were purchased from Integrated DNA Technologies, Inc. (Coralville, Iowa).

Isolation Procedure. One L of Aloe vera juice (Nature's Sunshine, Lot No. 9120378A) was filtered through a 0.2 µm membrane prior to use. Fractionation was accomplished using two consecutive ultrafiltration devices from Millipore (Bedford, Mass.). Low molecular weight material (<100,000 daltons) was removed by passing crude Aloe juice through a Centriplus-100 concentrator (15 mL volume) with a regenerated cellulose membrane. The retentate was then passed through a Centricon-500 concentrator (2 mL volume) with a regenerated cellulose membrane to remove all material with molecular weight less than 500,000 daltons.

Further purification of NP18298 from the high molecular weight aloe fraction (>500,000 daltons) employed size exclusion chromatography (SEC). The set-up consisted of a Model 600E system controller, UK6 injector, Model 600 solvent delivery system, Model 401 differential refractometer and a Model 3396A Hewlett-Packard integrator. Analysis was performed at a flow rate of 1 mL/minute using HPLC grade water and a Shodex Ohpak KB-805 SEC column (300 mm length×8 mm ID) held at 30° C. NP18298 polysaccharide fraction has an apparent molecular weight above 2 million daltons as estimated by comparison with the retention times from dextran standards (Sigma).

Structural Characterization. Carbohydrate composition of polysaccharide fraction NP18298 was estimated using a colorimetric assay based on reaction with phenol (5% w/v in water) and concentrated sulphuric acid. Absorbance was determined at 450 nm and 490 nm (see Sturgeon, R. J., In Methods in Plant Biochemistry; Dey, P. M., Harborne, J. B., Eds.; Academic Press: New York, 1990; Vol. 2, Chapter 1, pp 4–12).

Glycosyl composition and glycosyl linkage analysis was performed by The University of Georgia, Complex Carbohydrate Research Center. The glycosyl composition of the NP18298 polysaccharide fraction was determined using GC-mass spectrometry analysis of the TMS-methyl glycosides. NP18298 polysaccharide fraction (100 µg), containing 20 µg of internal standard myo-inositol, was hydrolyzed with 500 µL of 1.0M methanolic-HCl for 16 hours at 80° C. Excess methanolic-HCl was then evaporated at 40° C. with a stream of nitrogen. Additional methanol (250 µL) was added and the sample solution was dried down again. Released methylglycosides were N-acetylated using the following mixture: methanol (200 µL), pyridine (20 µL) and acetic anhydride (20 µL) for 15 min at 45° C. The acetylated sample was then dried down under a stream of nitrogen and trimethyl-sialylated (TMS) with 200 µL of Tril-Sil reagent at 80° C. for 20 min. Cooled sample was evaporated to dryness with a stream of nitrogen, dissolved in 100 µL of hexane and analyzed on a 30 m DB-1 column (0.25 mm×0.25 mm, i.d.; J & W Scientific, Folsom, Calif.) using a Hewlett Packard 5985 GC-MS system. The GC-MS temperature conditions were as follows: initial temperature of 160° C.; increased to 200° C. at 2°/min; and, a final increase to 260° C. at 10°/min. A standard of derivatized methylglycosides was also run along side the sample for identification of sugar units (see York, W. S.; Darvill, A. G.; McNeil, M.; Stevenson, T. T.; Albersheim, P., Methods Enzymol. 1986, 118, 3–40.)

For glycosyl linkage analysis, NP18298 (100 µg) was methylated using the Hakomori procedure, (see Hakomori, S., J. Biochem. Tokyo 1964, 55(2), 205–208), in combination with carboxyl-reduction in order to detect uronic acid linkages. Methylated material was isolated by extraction into methylene chloride, dried down and reduced with 500 µL of Superduteride for 3 hours at room temperature. The products were remethylated using the Hakomori method and then subjected to sequential hydrolysis with 2M TFA at 120° C. for 2 hours and subsequent reduction with 500 µL of 1M ammonium hydroxide solution containing 10 mg/mL of sodium borodeuteride at room temperature for 3 hours. The reduced sample was acetylated using acetic anhydride/pyridine at 120° C. for 3 hours. The resulting partially methylated alditol acetates were analyzed using a fused silica, 30 m Sp2330 column in a Hewlett-Packard 5985 GC-MS system with myo-inositol as an internal standard. The GC-MS temperature conditions were as follows: 2 minutes at an initial temperature of 80° C.; increased to 170° C. at 30° C./minute; and, a final increase to 240° C. at 40° C./minute and held there for 5 minutes (see Azadi, P.; O'Neill, M. A.; Bergmann, C.; Darvill, A. G.; Albersheim, P., *Glycobiology* 1995, 5(8), 783–789).

Macrophage Assay. Macrophage activation was measured using a luciferase reporter gene assay in THP-1 human monocytic cells. This assay measures immunostimulatory activity as indicated by increased expression of a NF-kappa B-driven luciferase reporter. THP-1 cells were cultured in RPMI 1640 medium supplemented with fetal bovine serum (10% v/v) and amikacin (60 mg/L) at 37° C., under 5% $CO_2$ and 95% air. Actively growing cells were transiently transfected using DEAE-dextran (see Selden, R. F., Short Protocols in Molecular Biology, 3rd Ed.; Ausubel, F. M., Brent, R., Kingston, R. E., Moore, D. D., Seidman, J. G., Smith, J. A., Struhl, K., Eds.; John Wiley & Sons: New York, 1995; 3rd Edition, pp 9–10–9–11) (10 µg/1×10$^6$ cells) and the pBIIXLUC reporter plasmid (1 µg/1×10$^6$ cells) containing two binding sites for NF-kappa B. Transfection solution containing THP-1 cells was incubated for 7 minutes in 37° C. water bath. The transfected cells were then resuspended in 10% FBS, RPMI 1640 medium and plated out in 96-well plates at a cell density of 2×10$^5$ cells per well. After 24-hours *aloe vera* extracts, fractions and NP18298 were added to transfected cells. Four hours after addition of samples, cells were harvested and luciferase activity measured. Cells were harvested used Packard filter plates and lysed using 30 µL of luciferase mix (1:1, LucLite™ luciferase:1×PBS, 1 mM Ca and Mg). Luciferase light emission was measured using a Packard microplate scintillation counter in single photon mode. Activation is reported as a percentage relative to maximal activation of NF-kappa B by 10 µg/mL LPS, used as a positive control.

Sequence of PCR primers. Sequences for the primers are described in Su, S.; Vivier, R. G.; Dickson, M. C.; Thomas, N.; Kendrick, M. K.; Williamson, N. M.; Anson, J. G.; Houston, J. G.; Craig, F. F. *BioTechniques* 1997, 22(6), 1107–1113.

IL-1β forward
(5'-ATG-GCA-GAA-GTA-CCT-AAG-CTC-GC-3');

IL-1β reverse
(5'-ACA-CAA-ATT-GCA-TGG-TGA-AGT-CAG-TT-3');

TNF-α forward
(5'-GAG-TGA-CAA-GCC-TGT-AGC-CCA-TGT-TGT-AGC-3');

TNF-α reverse
(5'-GCA-ATG-ATC-CCA-AAG-TAG-ACC-TGC-CCA-GAC-T-3');

GAPDH forward
(5'-TGA-AGG-TCG-GAG-TCA-ACG-GAT-TTG-GT-3');

GAPDH reverse
(5'-CAT-GTG-GGC-CAT-GAG-GTC-CAC-CAC-3').

RT-PCR for IL-1β, TNF-α and GAPDH. Actively growing THP-1 cells (3 mLs, 1×10$^6$ cells/mL) were incubated for 2 hours under the following conditions: control, LPS at 10 µg/mL, and NP18298 at 10 µg/mL. Total RNA was isolated using a TRI Reagent® kit in which cells are lysed using a combination of phenol and guanidine thiocyanate. After the addition of bromochloropropane, RNA is separated into the aqueous phase and subsequently precipitated with isopropanol. Total RNA recovered using this method is about 30 µg.

RT-PCR reactions were run using kit reagents from Promega. Each reaction used the following components (total volume of 30 µL): 6 µL AMV/Tfl 5×reaction buffer, 0.6 µL dNTP mix (10 mM), 1.2 µL $MgSO_4$ (25 mM), 0.6 µL AMV reverse transcriptase (5 units/µL), 0.6 µL Tfl DNA polymerase (5 units/µL), 1.2 µL of each primer (15 pmol/µL), and 2 ng total RNA (IL-1β, TNF-α) or 5 ng total RNA (GAPDH). The RT-PCR protocol used a Techne Unit Progene automatic thermal cycler. The first cycle consisted of 45 minutes at 48° C., followed by 2 minutes at 94° C. Amplification was achieved using 35 cycles: denature at 94° C. for 45 seconds, anneal at 60° C. for 1 minute, and extend at 68° C. for 2 minutes. The final cycle held samples at 68° C. for 7 minutes. Electrophoresis of RT-PCR products (mRNA IL-1β, TNF-α and GAPDH) was accomplished using 12 µL of reaction mix on 5% polyacrylamide gels and ethidium bromide as the staining agent.

DETAILED DESCRIPTION OF THE INVENTION

The transcription factor based bioassay for activation of NF-kappa B in THP-1 human monocytes/macrophages was used to evaluate and compare the immunostimulatory activity of crude *Aloe vera* juice and previously known compounds isolated from *Aloe vera*. Three major aloe anthraquinones (aloin, *aloe*-emodin and emodin) were inactive at 0.1 µg/mL, 1.0 µg/mL and 10 µg/mL. At higher concentrations they inhibited NF-kappa B directed luciferase expression (results not shown). Two different commercial polysaccharide preparations from *aloe*, were also evaluated: *Aloe vera* mucilaginous polysaccharide (AVMP) and Manapol. At 200 µg/mL AVMP exhibited 2.2% and Manapol exhibited 3.5% activation of NF-kappa B directed luciferase expression as compared with those achieved by maximal concentration of LPS at 10 µg/mL (see FIG. 1).

In contrast, two different Lots of crude whole leaf *Aloe vera* juice (Nature's Sunshine Products) at 200 µg/mL enhanced NF-kappa B activation by about 7% (see FIG. 1). Comparable levels of NF-kappa B activation was also observed with crude *Aloe vera* juice (4.2%) and *Aloe vera* gel (4.9%) from Lily of the Desert, also run at 200 µg/mL. It has been reported (see McAnalley, B. H., U.S. Pat. No. 4,735,935 (1988)) that acemannan comprises approximately 5% of the dry weight of *aloe* gel, and that very high concentrations of acemannan (e.g., 200 to 2000 µg/mL) are required to achieve modest activation of macrophages (see Karaca, K.; Sharma, J. M.; Nordgren, R., *Int. J. Immunopharmac*, 1995, 17(3), 183–188). Higher levels of macrophage activation can be achieved if acemannan is combined with other agents such as interferon-α (see Ramamoorthy, L.; Kemp, M. C.; Tizard, I. R., *Mol Pharmacol*. 1996, 50(4), 878–884). These results suggest that there is another component responsible for the observed level of NF-kappa B activation in crude *Aloe vera* juice.

Initial fractionation of crude whole leaf *Aloe vera* juice (Nature's Sunshine Products) was accomplished using two different ultrafiltration devices with molecular weight cut-off membranes of 100,000 and 500,000 daltons. The following three fractions were obtained for evaluation of immunostimulatory activity: first, extract material less than 100,000 daltons; second, extract material between 100,000 and 500,000 daltons; third, extract material greater than 500,000 daltons. The low molecular weight material (<100,000 daltons) was inactive at 50 μg/mL and the intermediate molecular weight material (100,000–500,000 daltons) displayed marginal NF-kappa B activation (15.4%) at 50 μg/mL (see FIG. 1). However, the high molecular weight material (>500,000 daltons) contained very potent activity (see FIG. 1). At 50 μg/mL this fraction increased NF-kappa B directed luciferase expression to levels equivalent to those achieved by maximal concentration of LPS (10 μg/mL).

The high molecular weight material (>500,000 daltons) was further fractionated using HPLC size exclusion chromatography. A typical chromatogram of this fraction (see FIG. 2a) gave two major peak regions: 5.0–5.5 minutes (apparent molecular weight above 2 million daltons), and 7.5–9.0 (estimated molecular weight between 0.1 and 1 million daltons). Both regions were evaluated for NF-kappa B activation and the first region (between 5.0 and 5.5 minutes) was at least 10 times more active than the second region (between 7.5 and 9.0 minutes). The single peak (see FIG. 2b) in the first region (NP18298) was isolated, through repeated injections, in sufficient quantity for structural characterization and immunostimulatory evaluation. NP18298 is a white powder and is soluble in water at 10 mg/mL. By comparison, AVMP and Manapol are very difficult to dissolve in water even at 1 mg/mL.

Chromatographic analysis of AVMP and Manapol preparations using the HPLC size exclusion separation system gave a major peak between 6.5 and 8.5 minutes (see FIGS. 2c and 2d) that agrees with previous studies. See Ross, S. A.; ElSohly, M. A.; Wilkins, S. P., *J AOAC Int.* 1997, 80(2), 455–457. The isolated fraction NP18298 (retention time between 5.0 and 5.5) is thus chromatographically distinct from these commercial preparations. Based on these chromatograms it is obvious that the molecular weight of NP18298 is much larger than the major substances present in AVMP or Manapol.

The amount of NP18298 represents about 0.015% of the crude *aloe* juice material (dry weight). This percentage is slightly higher due to the fact that a minor amount of NP18298 "leaked" through the 500,000 molecular weight cut-off ultrafiltration device (HPLC chromatogram not shown). Small amounts of NP18298 within the intermediate molecular weight fraction (100,000 to 500,000 daltons, see FIG. 1) would explain its low level of activity. The amount of "inactive" high molecular weight material between 0.1 and 1 million daltons (second region, see FIG. 2a) varies between 10% and 70% of the total area of all chromatographic peaks of this fraction, depending on the *Aloe vera* juice Lot preparation. This observation is in agreement with previous findings that report between 0 and 1.30 mg/mL of acemannan present in 18 different commercial *Aloe vera* products. See Ross, S. A.; ElSohly, M. A.; Wilkins, S. P., *J. AOAC Int.* 1997, 80(2), 455–457. This wide variability may be attributed to depolymerization (hydrolysis) of *aloe* polysaccharides that can occur in the presence of water and by the action of naturally occurring enzymes. See Farkas, A., U.S. Pat. No. 3,360,511, (1967).

FIG. 3 presents a dose response for both LPS and NP18298. The $EC_{50}$ (50% of maximal LPS induction) value for NF-kappa B directed luciferase expression for NP18298 is 0.5 μg/mL. To confirm THP-1 macrophage activation by NP18298, mRNA levels of proinflammatory cytokines IL-1β and TNF-α were measured using RT-PCR (see FIG. 4). Treatment of THP-1 cells with either LPS (10 μg/mL) or NP18298 resulted in a dramatic increase of both IL-1β mRNA (810 bp) and TNF-α mRNA (444 bp), as compared with the control. The mRNA levels of the housekeeping gene glyceraldehyde phosphate dehydrogenase (GAPDH, 1000 bp) was the same for all samples (see FIG. 4).

The observed NF-kappa B activation by NP18298 is not due to endotoxin. This was confirmed by testing for the presence of β-hydroxymyristate in the glycosyl composition analysis. In two separate sample preparations of NP18298, there were no detectable levels of β-hydroxymyristate. Thus, it is unlikely that the observed macrophage activation by NP18298 is due to endotoxins.

Using a colorimetric assay (see Sturgeon, R. J., In *Methods in Plant Biochemistry*; Dey, P. M., Harborne, J. B., Eds.; Academic Press: New York, 1990; Vol. 2, Chapter 1, pp 4–12) with phenol-sulphuric acid at 450 nm and 490 nm, the carbohydrate content of NP18298 was estimated between 80% and 100%. It is concluded from this result that NP18298 is a very high molecular weight polysaccharide fraction. Glycosyl composition and glycosyl linkage analysis for NP18298 is summarized in Table 1 (see below). The major glycosyl components are glucose (37.2%), galactose (23.9%), mannose (19.5%) and arabinose (10.3%). For linkage analysis, the major derivatives included 1,6-linked glucose (24.2%), 1,4-linked mannose (19.2%) and 3,6-linked galactose (11.2%). Although the polysaccharide was methylated by a protocol designed to detect uronic acid linkages, no such glycosyl linkages were observed. However, if the glucuronic acid was present as a methyl ester, it would have been destroyed during the methylation procedure.

TABLE 1

Glycosyl Composition and Glycosyl Linkage Data for Isolated Aloe Vera Polysaccharide Fraction NP18298. The data was obtained from one experiment.

| Glycosyl Residue | Mole % | Glycosyl Linkage | % total area |
|---|---|---|---|
| glucose | 37.2 | 1,6-linked glucose | 24.2 |
| galactose | 23.9 | 1,4-linked mannose | 19.2 |
| mannose | 19.5 | 3,6-linked galactose | 11.2 |
| arabinose | 10.3 | terminal 1-glucose | 7.6 |
| rhamnose | 5.8 | 3-linked galactose | 6.4 |
| glucuronic acid | 3.3 | T 1-arabinofuranose | 5.1 |
| | | terminal 1-galactose | 4.5 |
| | | 1,6-linked galactose | 4.3 |
| | | 3,6-linked glucose | 3.8 |
| | | 1,4-Araf or 1,5-Arap | 2.1 |
| | | terminal 1-rhamnose | 1.8 |
| | | 1,4-linked glucose | 1.8 |
| | | 4,6-linked glucose | 1.4 |
| | | 3,4-linked galactose | 1.3 |
| | | 3-linked glucose | 1.1 |
| | | 3,4,6-linked galactose | 0.9 |
| | | Terminal mannose | 0.8 |
| | | 4,6-linked mannose | 0.8 |
| | | 3-linked arabinofuranose | 0.7 |
| | | Terminal arabinopyranose | 0.6 |
| | | 4,6-linked galactose | 0.4 |

The structure of acemannan consists of a polydispersed β-(1,4)-linked acetylated mannan interspersed with O-acetyl groups. The degree of acetylation is about 0.91 acetyl groups per monomer. The ratio between mannose and galactose is about 20:1 (see McAnalley, B. H.; Carpenter, R. H.; McDaniel, H. R., U.S. Pat. No. 5,468,737 (1995)). Although NP18298 contains 1,4-linked mannose (19.2%), it also has a variety of other major sugar units that exist only as minor constituents in acemannan.

A number of other polysaccharides isolated from *Aloe vera* have been published in the patent literature. For example, a polyuronide with a molecular weight between 275,000 and 374,000 is reported to be useful in treatment of surface wounds (see Farkas, A., U.S. Pat. No. 3,103,466 (1963)). The 70KD polysaccharide, Aloeferon, has also been reported to have therapeutic potential (see Madis, V. H.; Omar, M. M.; Madis, V., U.S. Pat. No. 4,861,761 (1989)). Other active components isolated from *aloe* include a polysaccharide between 420,000 and 520,000 daltons comprised of equal amounts of glucose and mannose (see Farkas, A., U.S. Pat. No. 3,362,951 (1968)). In addition, several groups have enzymatically prepared altered polysaccharide compositions from the naturally occurring carbohydrates in *aloe* (see Strickland, F. M.; Pelley, R. P.; Kripke, M. L., U.S. Pat. No. 5,824,659 (1998)). Clearly, NP18298 is a new polysaccharide fraction that is distinctly different both in molecular weight and glycosyl composition from any of these other *aloe* polysaccharide preparations that have been isolated or prepared.

In summary, the present invention relates to the isolation of a new high molecular weight polysaccharide fraction (NP18298) from commercial *Aloe vera* juice that is chemically distinct in both molecular weight and glycosyl composition/linkage from any *aloe* polysaccharide material previously isolated. In the NF-kappa B transcription factor-based bioassay, NP18298 robustly activates THP-1 macrophages. Although this polysaccharide comprises only 0.015% of the original dry weight, its potency in this assay accounts fully for the activity observed in the crude *aloe* juice. Pharmaceutical development of NP18298 as an immunostimulant, either alone or in combination with other *aloe* components, may have significant potential for wound healing and immunotherapy. Polysaccharide fraction NP18298 could also be valuable for standardization of commercial *aloe* products. The research in this invention could also be used to develop new *aloe* products that are enriched for immune enhancing properties by concentrating the levels of NP18298.

The instant polysaccharide fraction has superior macrophage stimulatory activity compared with clinically used polysaccharide preparations. It would therefore be useful as an agent for immunotherapy in the treatment of immunodeficiency disorders, cancer, wound healing and infectious diseases. The present invention includes pharmaceutical compositions containing the instant polysaccharide fraction, optionally in combination with acceptable pharmaceutical carriers or excipients.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

The amount of composition administered will be dependent upon the condition being treated, the subject being treated, on the subject's weight, the severity of the affliction, the manner of administration and the judgment of the individual's physician.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the compositions and compounds into preparations which can be used pharmaceutically. Proper formulation is dependent upon the route of administration chosen.

For injection, the agents of the invention may be formulated in aqueous solutions, preferably in physiologically compatible buffers such as Hanks solution, Ringers solution, or physiological saline buffer. For transmucosal administration, penetrants appropriate to the barrier to be permeated are used in the formulation. Such penetrants are generally known in the art.

For oral administration, the compositions can be formulated readily by combining the active compositions with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

If desired, disintegrating agents may be added, such as the cross-linked polyvinyl pyrrolidone, agar, or alginic acide or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a power mix of the compound and a suitable powder base such as lactose or starch.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active composition may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compositions may also be formulated in rectal compositions such as suppositories or retention enemas, e.g., containing conventional suppository bases such as cocoa butter or other glycerides.

In addition to the formulations described previously, the compositions may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable routes of administration may, for example, include oral, rectal, transmucosal, transdermal, or intestinal administration, parenteral delivery, including intramuscular, subcutaneous, intramedullary injections, as well as intrathecal, direct intraventricular, intravenouse, intraperitoneal, intranasal, or intraocular injections.

Alternatively, one may administer the composition in a local rather than systemic manner, for example, via injection of the compound directly into an affected area, often in a depot or sustained release formulation.

Furthermore, one may administer the drug in a targeted drug delivery system, for example, in a liposome coated with an antibody specific for affected cells. The liposomes will be targeted to and taken up selectively by the cells.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a composition of the invention formulated in a compatible pharmaceutical carrier may also be prepared, placed in an appropriate container, and labeled for treatment of an indicated condition. Suitable conditions indicated on the label may include treatment of a disease.

The present polysaccharide fraction is also useful as a component of a dietary supplement. Dietary supplements suitable for use in the present invention include compositions wherein the active ingredients are contained in an effective amount to achieve its intended purpose. More specifically, an effective amount means an amount effective to prevent development of or to alleviate the existing symptoms of the subject being treated. Determination of the effective amounts is well within the capability of those skilled in the art, especially in light of the detailed disclosure provided herein. The amount of composition administered will be dependent upon the condition being treated, the subject being treated, on the subject's weight, the severity of the affliction, the manner of administration and the judgment of the individual's physician.

The ingredients of the dietary supplement of this invention are contained in acceptable excipients and/or carriers for oral consumption. The actual form of the carrier, and thus, the dietary supplement itself, may not be critical. The carrier may be a liquid, gel, gelcap, capsule, powder, solid tablet (coated or non-coated), tea or the like. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, agar, lactose, methylcellulose, povidone, carboxymethylcellulose, corn starch, and the like (including mixtures thereof). The various ingredients and the excipient and/or carrier are mixed and formed into the desired form using conventional techniques. Dose levels/unit can be adjusted to provide the recommended levels of ingredients per day in a reasonable number of units.

The dietary supplement may also contain optional ingredients including, for example, herbs, vitamins, minerals, enhancers, colorants, sweeteners, flavorants, inert ingredients, and the like. Such optional ingredients may be either naturally occurring or concentrated forms. Selection of one or several of these ingredients is a matter of formulation, design, consumer preference and end-user. The amounts of these ingredients added to the dietary supplements of this invention are readily known to the skilled artisan. Guidance to such amounts can be provided by the U.S. RDA doses for children and adults.

All references mentioned above are expressly incorporated by reference into the present application.

What is claimed is:

1. A water soluble immunostimulatory *Aloe vera* polysaccharide fraction isolated from *Aloe vera*, said *Aloe vera* polysaccharide having an apparent molecular weight of over 2 million daltons and contains the glycosyl components glucose, galactose, mannose and arabinose.

2. The polysaccharide fraction of claim 1 where the immunostimulation is manifested by monocyte/macrophage activation.

3. A pharmaceutical composition comprising the polysaccharide fraction of claim 1 in a pharmaceutically acceptable carrier or excipient.

4. A dietary supplement composition comprising the polysacharide fraction of claim 1 in a carrier or excipient consistent with dietary supplements.

5. A method of providing immunostimulation in an individual in need of such treatment comprising administering to said individual an effective amount of the composition of claim 1.

6. The method of claim 5 wherein the individual is being treated for immune deficiency.

7. The method of claim 5 wherein the individual is being treated for cancer.

8. The method of claim 5 wherein the individual is being treated for a bacterial, viral or fungal infection.

9. The method of claim 5 wherein the individual is being treated for wound healing.

10. The method of claim 5 wherein the individual is a human being.

11. The method of claim 5 wherein the individual is an animal.

12. A method of providing immunostimulation in an individual of need of such treatment comprising administrating to said individual an effective amount of the dietary supplement composition of claim 4.

13. The method of claim 12 wherein the individual is being treated for immune deficiency.

14. The method of claim 12 wherein the individual is being treated for cancer.

15. The method of claim 12 wherein the individual is being treated for a bacterial, viral or fungal infection.

16. The method of claim 13 wherein the individual is being treated for wound healing.

17. The method of claim 13 wherein the individual is a human being.

18. The method of claim 13 wherein the individual is an animal.

* * * * *